United States Patent [19]

Rubin et al.

[11] Patent Number: 5,026,943
[45] Date of Patent: Jun. 25, 1991

[54] CATALYTIC CONVERSION OVER CATALYST COMPRISING SYNTHETIC CRYSTAL MCM-35

[75] Inventors: Mae K. Rubin, Bala Cynwyd, Pa.; Pochen Chu, Voorhees, N.J.

[73] Assignee: Mobil Oil Corp, Fairfax, Va.

[21] Appl. No.: 587,837

[22] Filed: Sep. 25, 1990

Related U.S. Application Data

[63] Continuation-in-part of Ser. No. 471,173, Jan. 26, 1990, Pat. No. 4,981,663, which is a continuation-in-part of Ser. No. 191,528, May 9, 1988, abandoned.

[51] Int. Cl.$^5$ .............................................. C07C 63/34
[52] U.S. Cl. ...................................... 585/467; 208/46; 208/108; 208/111; 208/120; 208/135
[58] Field of Search .................. 208/46, 111, 120, 135, 208/108; 585/467

[56] References Cited

U.S. PATENT DOCUMENTS

| | | | |
|---|---|---|---|
| 2,904,607 | 9/1959 | Mattox et al. | 260/671 |
| 3,251,897 | 5/1966 | Wise | 260/671 |
| 3,631,120 | 12/1971 | Eberly, Jr. et al. | 260/671 |
| 3,641,177 | 2/1972 | Eberly, Jr. et al. | 260/671 C |
| 3,751,504 | 8/1973 | Keown et al. | 260/672 T |
| 3,751,506 | 8/1973 | Burress | 260/671 R |
| 3,755,483 | 4/1972 | Burress | 260/671 R |
| 4,393,262 | 7/1983 | Kaeding | 585/467 |
| 4,469,908 | 9/1984 | Burress | 585/467 |
| 4,559,131 | 12/1985 | Miale | 208/111 |
| 4,620,921 | 11/1986 | Chang et al. | 208/111 |

OTHER PUBLICATIONS

Petrochemical Preprings, American Chemical Society, vol. 22, No. 3, p. 1084 (1977).

Primary Examiner—Helane E. Myers
Attorney, Agent, or Firm—Alexander J. McKillop; Charles J. Speciale; Lori F. Cuomo

[57] ABSTRACT

This invention relates to catalytic conversion of organic compounds over MCM-35, a new crystalline material exhibiting a distinctive X-ray diffraction pattern. The conversion process includes the mechanisms of cracking, hydrocracking, dewaxing, dehydrogenation and aromatic alkylation.

32 Claims, No Drawings

CATALYTIC CONVERSION OVER CATALYST COMPRISING SYNTHETIC CRYSTAL MCM-35

CROSS-REFERENCE TO RELATED APPLICATIONS

This is a continuation-in-part of application Ser. No. 471,173, filed Jan. 26, 1990 now U.S. Pat. No. 4,981,663, which is a continuation-in-part of application Ser. No. 191,528, filed May 9, 1988, now abandoned.

BACKGROUND OF THE INVENTION

This invention relates to use of a novel synthetic crystalline material for catalytic conversion of organic compounds, non-limiting examples of which include conversion of hydrocarbon compound feedstock to product having a lower molecular weight than said feedstock, and alkylation of aromatic compounds.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as $Ca/2$, $Sr/2$, Na, K or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic zeolites. The zeolites have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), ZSM-35 (U.S. Pat. No. 4,016,245), ZSM-38 (U.S. Pat. No. 4,046,859), and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6 In some zeolites, the upper limit of the $SiO_2/Al_2O_3$ ratio is u-bounded ZSM-5 is one such example wherein the $SiO_2/Al_2O_3$ ratio is greater than 5 and up to infinity. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates or organosilicates of varying alumina and metal content.

Alkylation is one of the most important and useful reactions of hydrocarbons. Lewis and Bronsted acids, including a variety of natural and synthetic zeolites, have been used as catalyst. Alkylation of aromatic hydrocarbon compounds employing certain crystalline zeolite catalysts is known in the art. For instance, U.S. Pat. No. 3,251,897 describes liquid phase alkylation in the presence of crystalline aluminosilicates such as faujasite, heulandite, clinoptilolite, mordenite, dachiardite, zeolite X and zeolite Y. The temperature of such alkylation procedure does not exceed 600° F., thereby maintaining patentee's preferable operating phase as substantially liquid.

Also, U.S. Pat. No. 2,904,607 shows alkylation of hydrocarbon compounds in the presence of certain crystalline zeolites. The zeolites described for use in this patent are crystalline metallic aluminosilicates, such as, for example, magnesium aluminosilicate.

U.S. Pat. Nos. 3,631,120 and 3,641,177 describe liquid phase processes for alkylation of aromatic hydrocarbons with olefins in the presence of certain zeolites. U.S. Pat. No. 3,631,120 discloses use of an ammonium exchanged, calcined zeolite having a silica to alumina mole ratio of between 4.0 and 4.9. U.S. Pat. No. 3,641,177 discloses use of a zeolite catalyst activated in a particular manner.

U.S. Pat. Nos. 3,751,504 and 3,751,506 describe the vapor phase alkylation of aromatic hydrocarbons with olefins in the presence of a specified type of zeolite catalyst.

U.S. Pat. Nos. 3,755,483 and 4,393,262 disclose the vapor phase reaction of propylene with benzene in the presence of zeolite ZSM-12, to product isopropylbenzene.

U.S. Pat. No. 4,469,908 discloses the alkylation of aromatic hydrocarbons with relatively short chain alkylating agents having from one to five carbon atoms employing ZSM-12 as alkylation catalyst.

Harper et al. have described catalytic alkylation of benzene with propylene over a crystalline zeolite (Petrochemical Preprints, American Chemical Society, Vol. 22, No. 3, p. 1084, 1977). Extensive kinetic and catalyst aging studies were conducted with a rare earth exchanged Y-type zeolite (REY) catalyst.

U.S. Pat. Nos. 4,559,131 and 4,620,921 claim use of various catalysts for converting feedstock comprising hydrocarbon compounds to conversion product comprising hydrocarbon compounds of lower molecular weight than feedstock hydrocarbon compounds.

SUMMARY OF THE INVENTION

The present invention is directed to use of a novel crystalline material designated "MCM-35", as a catalyst component for conversion of organic compounds contacted therewith. It is a particular object of this invention to provide a process for converting a hydrocarbon feedstock to product of lower molecular weight than the feedstock, such as, for example, by cracking, hydrocracking, dewaxing and dehydrogenation.

It is a further particular object of the present invention to provide a process for alkylation of an aromatic compound with a relatively short chain alkylating agent to produce a short chain alkyl aromatic product employing alkylation catalyst comprising synthetic porous crystalline MCM-35.

Another particular object of the present invention is to provide a process for alkylating benzene with propylene to produce cumene, or with ethylene to produce ethylbenzene, with limited by-product, e.g. xylenes, make.

It is another particular object of the present invention to provide a process for the alkylation of reformate with fuel gas or other source of light olefins to produce an alkylate reformate product containing, inter alia, short chain mono- and dialkylates.

The structure of the crystalline material MCM-35 is distinguished from other crystalline materials by a unique X-ray diffraction pattern. A typical X-ray diffraction pattern for this material includes the lines shown in Table 1, hereinafter.

EMBODIMENTS

The crystalline material catalyst component for use in this invention has a composition involving the molar relationship:

$$X_2O_3:(n)YO_2$$

wherein X is a trivalent element, such as aluminum, boron, iron and/or gallium, preferably aluminum, Y is a tetravalent element such as silicon and/or germanium, preferably silicon, and n is at least about 30, usually from about 40 to about 200, more usually from about 60 to about 150. In the as-synthesized form, the material has a formula, on an anhydrous basis and in terms of moles of oxides per n moles of $YO_2$, as follows:

$$(0.1-0.8)M_2O:(0.5-4)R_2O:X_2O_3:nYO_2$$

wherein R is an organic and M is alkali metal. The M and R components are associated with the material as a result of their presence during crystallization, and are easily removed by post-crystallization methods hereinafter more particularly described.

The original cations, e.g. alkali metal, of the as-synthesized material can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which render the material catalytically active, especially for the hydrocarbon conversion reaction mechanisms of this invention. These include hydrogen, rare earth metals and metals of Groups IIA, IIIA, IVA, IB, IIB, IIIB, IVB and VIII of the Periodic Table of the Elements.

Typical ion exchange technique would be to contact the synthetic material with a salt of the desired replacing cation or cations. Examples of such salts include the halides, e.g. chlorides, nitrates and sulfates.

Crystals of MCM-35 have an X-ray diffraction pattern which distinguishes it from other crystalline materials. The X-ray diffraction pattern of MCM-35 includes the following significant lines:

TABLE 1

| Interplanar d-Spacing (A) | Relative Intensity, I/Io |
|---|---|
| 15.4 ± 0.23 | mw-m |
| 9.03 ± 0.14 | mw-ms |
| 6.62 ± 0.10 | w-mw |
| 4.99 ± 0.07 | mw-m |
| 4.04 ± 0.05 | m-ms |
| 3.31 ± 0.04 | mw-m |
| 2.00 ± 0.03 | mw-m |

These X-ray diffraction data and those of the following specific examples were collected with a Philips diffraction system, equipped with a graphite diffracted beam monochromator and scintillation counter, using copper K-alpha radiation. The diffraction data were recorded by step-scanning at 0.04 degrees of two-theta, where theta is the Bragg angle, and a counting time of 4 seconds for each step. The interplanar spacings, d's, were calculated in Angstrom units (A), and the relative intensities of the lines, I/Io, where Io is one-hundredth of the intensity of the strongest line, above background, were derived with the use of a profile fitting routine (or second derivative algorithm). The intensities are uncorrected for Lorentz and polarization effects. The relative intensities are given in terms of the symbols vw=very weak (0-5), w=weak (5-10) mw=medium weak (10-20), m=medium (20-40), ms=medium strong (40-60), s=strong (60-80) and vs=very strong (80-100). It should be understood that diffraction data listed for this sample as single lines may consist of multiple overlapping lines which under certain conditions, such as differences in crystallite sizes or very high experimental resolution or crystallographic changes, may appear as resolved or partially resolved lines. Typically, crystallographic changes can include minor changes in unit cell parameters and/or a change in crystal symmetry, without a change in topology of the structure. These minor effects, including changes in relative intensities, can also occur as a result of differences in cation content, framework composition, nature and degree of pore filling, and thermal and/or hydrothermal history.

Since MCM-35 has a plate-like morphology, experimental or measured intensity distortions due to preferred orientation are possible. This was taken into account in the above analysis and is reflected accurately by Table 1.

The crystalline material for use in the present invention can be used either in the alkali metal form, e.g. the sodium or potassium form; the ammonium form; the hydrogen form or another univalent or multivalent cationic form. When used as a catalyst, the material may be subjected to thermal treatment.

MCM-35, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product is particularly useful in the catalysis of certain hydrocarbon conversion reactions.

When employed either as an adsorbent or as a catalyst component in an organic compound conversion process, MCM-35 should be dehydrated, at least partially. This can be done by heating to a temperature in the range of 200° C. to 595° C. in an inert atmosphere, such as air, nitrogen, etc. and at atmospheric, subatmospheric or superatmospheric pressures for between 30 minutes and 48 hours. Dehydration can also be performed at room temperature merely by placing the material in a vacuum, but a longer time is required to obtain a sufficient amount of dehydration.

MCM-35 can be prepared from a reaction mixture containing sources of alkali metal cation, an oxide of trivalent element X, e.g. aluminum, an oxide of tetravalent element Y, e.g. silicon, an organic (R) directing agent, e.g. hexamethyleneimine, and water, said reaction mixture having a composition, in terms of mole ratios of oxides, within the following ranges:

| Reactants | Useful | Preferred |
|---|---|---|
| $YO_2/X_2O_3$ | 30 to 200 | 50 to 150 |
| $H_2O/YO_2$ | 10 to 100 | 15 to 40 |
| $OH^-/YO_2$ | 0.01 to 0.20 | 0.02 to 0.10 |
| $M/YO_2$ | 0.01 to 1.0 | 0.05 to 0.3 |
| $R/YO_2$ | 0.1 to 1.0 | 0.1 to 0.5 |

Crystallization of MCM-35 can be carried out at either static or stirred conditions in a suitable reactor vessel, such as for example, polypropylene jars or teflon lined or stainless steel autoclaves. The total useful range of temperatures for crystallization is from about 80° C. to about 250° C. for a time sufficient for crystallization to occur at the temperature used, e.g. from about 24 hours to about 20 days. Thereafter, the crystals are separated from the liquid and recovered. The reaction mixture can be prepared utilizing materials which supply the appropriate components.

Where $YO_2$ is silica, the silica sources such as those containing at least about 30 wt. % solid silica, e.g. Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) may be used. Other sources of silica include Q-Brand (a sodium silicate comprised of about 28.8 wt. % $SiO_2$, 8.9 wt. % $Na_2O$ and 62.3 wt. % $H_2O$). Preferably, the silica source will contain at least about 80 wt. % solid silica, and more preferably at least about 85 wt. % solid silica.

It should be realized that the crystal synthesis reaction mixture components can be supplied by more than one source. The reaction mixture can be prepared either batchwise or continuously. Crystal size and crystallization time of the new crystalline material will vary with the nature of the reaction mixture employed and the crystallization conditions.

In all cases, synthesis of MCM-35 crystals is facilitated by the presence of at least 0.01 percent, preferably 0.10 percent and still more preferably 1 percent seed crystals (based on total weight) of crystalline product.

The MCM-35 crystals can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

MCM-35 can be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be exchanged into the composition, e.g. to the extent aluminum is in the structure, impregnated therein or intimately physically admixed therewith. Such component can be impregnated in or on to it such as, for example in the case of platinum, by treating the crystalline material with a solution containing a platinum metal containing ion. Thus, suitable platinum compounds include chloroplatinic acid, platinous chloride and various compounds containing the platinum amine complex.

In general, feedstocks to the present process include straight and slightly branched wax components, e.g. paraffins, of up to about 50 carbon atoms per molecule and aromatic compounds. The term "aromatic" is used to include alkyl-substituted and unsubstituted mono- and polynuclear compounds. Compounds of an aromatic character which possess a heteroatom are also useful, provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, toluene, xylene, naphthalene, anthracene, naphthacene, perylene, coronene and phenanthrene.

Generally, the alkyl groups which can be present as substituents on the aromatic compound contain from one to about twenty-two carbon atoms and preferably from about one to eight carbon atoms, and most preferably from about one to four carbon atoms.

Suitable alkyl-substituted aromatic compounds include toluene; xylene; isopropylbenzene; normal propylbenzene; alpha-methylnaphthalene; ethylbenzene; cumene; mesitylene; durene; p-cymene; butylbenzene; pseudocumene; o-diethylbenzene; m-diethylbenzene; p-diethylbenzene; isoamylbenzene; isohexylbenzene; pentaethylbenzene; pentamethylbenzene; 1,2,3,4-tetraethylbenzene; 1,2,3,5-tetramethylbenzene; 1,2,4-triethylbenzene; 1,2,3-trimethylbenzene; m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methylphenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes.

Reformate containing substantial quantitites of benzene, toluene and/or xylene constitutes a particularly useful feed for the alkylation process of this invention.

The alkylating agents which are useful in the process of this invention generally include any organic compound having at least one available alkylating group capable of reaction with the alkylatable aromatic compound, the alkylating group possessing from 1 to 5 carbon atoms. Examples of suitable alkylating agents are olefins such as ethylene, propylene, the butenes and the pentenes; alcohols (inclusive of monoalcohols, dialcohols, trialcohols, etc.) such as methanol, ethanol, the propanols, the butanols and the pentanols; aldehydes such as formaldehyde, acetaldehyde, propionaldehyde, butyraldehyde and n-valeraldehyde; and alkyl halides such as methyl chloride, ethyl chloride, the propyl chlorides, the butyl chlorides and the pentyl chlorides, and so forth.

Mixtures of light olefins are especially useful as alkylating agents in the alkylation process of this invention. Accordingly, mixtures of ethylene, propylene, butenes and/or pentenes which are major constituents of a variety of refinery streams, e.g. fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt. % | Mole % |
|---|---|---|
| Ethane | 3.3 | 5.1 |
| Ethylene | 0.7 | 1.2 |
| Propane | 14.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

In general, reaction conditions for the present process include a temperature of from about 0° C. to about 800° C., a pressure of from about 0.1 atmosphere (bar) to about 250 atmospheres, and a weight hourly space velocity (WHSV) of from about 0.08 hr$^{-1}$ 500 hr$^{-1}$.

When organic compounds such as, for example, hydrocarbons are converted to conversion products such as, for example, lower molecular weight hydrocarbons, over catalyst comprising MCM-35, the conversion conditions include a temperature of from about 100° C. to about 800° C., a pressure of from about 0.1 atmosphere (bar) to about 100 atmospheres, a weight hourly space velocity of from about 0.08 hr$^{-1}$ to about 20 hr$^{-1}$ and a hydrogen/feedstock organic, e.g. hydrocarbon, compound mole ratio of from 0 (no added hydrogen) to about 100.

Such conversion processes include, as non-limiting examples, cracking hydrocarbons to lower molecular weight hydrocarbons with reaction conditions including a temperature of from about 300° C. to about 800° C., a pressure of from about 0.1 atmosphere (bar) to about 35 atmospheres and a weight hourly space velocity of from about 0.1 to about 20 hr$^{-1}$; and dehydrogenating hydrocarbon compounds with reaction conditions including a temperature of from about 300° C. to about 700° C., a pressure of from about 0.1 atmosphere to about 10 atmospheres and a weight hourly space velocity of from about 0.1 to about 20 hr$^{-1}$.

When organic compounds such as aromatics are converted by alkylation over catalyst comprising MCM-35, the alkylation conversion conditions include a temperature of from about 0° C. to about 500° C., preferably from about 50° C. to about 250° C., a pressure of from about 0.2 atmosphere to about 250 atmospheres, preferably from about 1 atmosphere to about 25 atmospheres, a WHSV of from about 0.1 hr$^{-1}$ to about 500 hr$^{-1}$, preferably from about 0.5 hr$^{-1}$ to about 100 hr$^{-1}$ and an alkylatable aromatic compound/alkylating agent molar ratio of from about 0.1 to about 50, preferably from about 0.5 to about 15.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e. combined therewith, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powderlike materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented. In the examples all percentages are by weight, and whenever sorption data are set forth for comparison of sorptive capacities for cyclohexane, water and/or hexane, they were determined as follows:

A weighed sample of the calcined adsorbant was contacted with the desired pure adsorbate vapor in an adsorption chamber, evacuated to less than 1 mm and contacted with 12 mm Hg of water vapor or 40 mm Hg of n-hexane or cyclohexane vapor, pressures less than the vapor-liquid equilibrium pressure of the respective adsorbate at 90° C. The pressure was kept constant (within about ±0.5 mm) by addition of adsorbate vapor controlled by a manostat during the adsorption period, which did not exceed about 8 hours. As adsorbate was adsorbed by the new crystal, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec$^{-1}$) The Alpha Test is described in U.S. Pat. No. 3,354,078, in *The Journal of Catalysis*, Vol. 4, pp. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

EXAMPLE 1

A 30 g quantity of $Al_2(SO_4)_3 \cdot xH_2O$ was dissolved in a solution containing 56.8 g of 45% KOH and 1235 g of water. A 236 g quantity of a precipitated, spray dried silica containing about 90% silica (i.e. Ultrasil) was added to the solution and the total was mixed thoroughly. Finally, 105 g of hexamethyleneimine was added to the mixture with thorough agitation. The resulting reaction mixture had the following composition, in mole ratios:

| | | |
|---|---|---|
| $SiO_2/Al_2O_3$ | = | 70.0 |
| $H_2/SiO_2$ | = | 19.9 |
| $OH^-/SiO_2$ | = | 0.043 |
| $K/SiO_2$ | = | 0.13 |
| $R/SiO_2$ | = | 0.30 | wherein R is hexamethyleneimine.

This mixture was then crystallized in a stirred reactor at 175° C. for 3 days. The product crystals were recovered by filtration, washed with water and then dried at 120° C. A portion of the dried product was submitted for X-ray and chemical analysis. X-ray analysis identified the product crystals as the new crystalline material of this invention, with the X-ray powder diffraction pattern including the lines presented in Table 2.

TABLE 2

X-RAY DIFFRACTION PATTERN OF THE DRIED PRODUCT OF EXAMPLE 1

| Observed 2 Theta | d (A) | Relative Intensity |
|---|---|---|
| 5.78 | 15.29 | 11 |
| 9.74 | 9.08 | 17 |
| 11.53 | 7.68 | 1 |
| 13.39 | 6.61 | 6 |
| 15.38 | 5.76 | 9 |
| 16.72 | 5.30 | 1 |
| 17.32 | 5.12 | 6 |
| 17.81 | 4.98 | 19 |
| 18.73 | 4.74 | 1 |
| 19.58 | 4.53 | 2 |
| 21.25 | 4.18 | 53 |
| 22.01 | 4.04 | 39* |
| 22.31 | 3.98 | 40 |
| 22.74 | 3.91 | 76 |
| 24.31 | 3.66 | 4 |
| 25.04 | 3.56 | 13 |
| 25.59 | 3.48 | 100 |
| 25.99 | 3.43 | 30 |
| 26.54 | 3.36 | 13** |
| 26.97 | 3.31 | 25 |
| 27.86 | 3.20 | 6 |
| 28.13 | 3.17 | 15 |
| 29.02 | 3.08 | 3 |
| 29.57 | 3.03 | 13 |
| 30.21 | 2.958 | 11 |
| 31.31 | 2.856 | 6 |
| 31.68 | 2.824 | 11 |
| 32.48 | 2.756 | 3 |
| 33.00 | 2.714 | 4 |
| 33.40 | 2.682 | 5 |
| 34.45 | 2.603 | 3 |
| 34.93 | 2.568 | 2 |
| 35.71 | 2.514 | 2 |
| 36.80 | 2.442 | 4 |
| 37.07 | 2.425 | 6 |
| 37.34 | 2.408 | 8 |
| 37.87 | 2.376 | 5 |
| 38.30 | 2.250 | 5 |
| 39.26 | 2.294 | 3 |
| 39.89 | 2.260 | 3 |
| 40.49 | 2.228 | 3 |
| 41.14 | 2.194 | 3 |
| 41.95 | 2.154 | 4 |
| 42.60 | 2.122 | 2 |
| 43.46 | 2.082 | 5 |
| 43.94 | 2.061 | 3 |
| 45.23 | 2.005 | 21* |
| 46.30 | 1.961 | 5 |
| 46.95 | 1.935 | 11 |
| 48.60 | 1.873 | 6 |
| 50.10 | 1.821 | 5 |
| 51.02 | 1.790 | 5 |
| 51.72 | 1.768 | 5 |
| 52.46 | 1.744 | 4 |
| 53.00 | 1.728 | 7 |
| 53.87 | 1.702 | 5 |
| 55.43 | 1.658 | 4 |
| 57.24 | 1.609 | 4 |
| 58.16 | 1.586 | 5 |
| 59.22 | 1.560 | 4 |

In Table 2, * indicates that a shoulder appears on the low 2 Theta side of the peak, and ** indicates that a shoulder appears on the high 2 Theta side of the peak. There was an indication of a very small amount of impurity in this sample.

The chemical composition of the product of Example 1 was as follows, in weight percent:

| | |
|---|---|
| N | 0.93 |
| K | 0.49 |
| $Al_2O_3$ | 2.4 |
| $SiO_2$ | 86.0 |
| Ash | 94.9 |

-continued

| | |
|---|---|
| SiO$_2$/Al$_2$O$_3$, molar | 60.9 |

A portion of the crystalline product of this example was calcined at 538° C. for 6 hours in air and submitted for sorption and X-ray analysis. The X-ray powder diffraction pattern of the calcined material included the lines presented in Table 3.

TABLE 3

X-RAY DIFFRACTION PATTERN OF THE CALCINED PRODUCT OF EXAMPLE 1

| Observed 2 Theta | d (A) | Relative Intensity |
|---|---|---|
| 5.75 | 15.36 | 22 |
| 9.79 | 9.03 | 31 |
| 11.48 | 7.71 | 3 |
| 12.09 | 7.32 | 3 |
| 12.75 | 6.94 | 2 |
| 13.37 | 6.62 | 12* |
| 15.40 | 5.75 | 2 |
| 17.37 | 5.11 | 3 |
| 17.79 | 4.99 | 16 |
| 18.73 | 4.74 | 2 |
| 19.56 | 4.54 | 1 |
| 21.26 | 4.18 | 52 |
| 22.02 | 4.04 | 41* |
| 22.32 | 3.98 | 32 |
| 22.79 | 3.90 | 66 |
| 24.35 | 3.66 | 4 |
| 25.04 | 3.56 | 47 |
| 25.54 | 3.49 | 100 |
| 26.01 | 3.43 | 30 |
| 26.54 | 3.35 | 12 |
| 26.95 | 3.31 | 23** |
| 27.84 | 3.20 | 6 |
| 28.18 | 3.17 | 16 |
| 29.53 | 3.03 | 11 |
| 30.13 | 2.966 | 11 |
| 31.36 | 2.852 | 8 |
| 31.73 | 2.820 | 12 |
| 32.50 | 2.755 | 3 |
| 32.98 | 2.716 | 4 |
| 33.45 | 2.679 | 5 |
| 33.84 | 2.649 | 2 |
| 34.49 | 2.600 | 2 |
| 34.96 | 2.568 | 2 |
| 35.71 | 2.514 | 1 |
| 36.80 | 2.442 | 4 |
| 37.29 | 2.411 | 8 |
| 37.94 | 2.372 | 4 |
| 38.36 | 2.346 | 3 |
| 39.27 | 2.294 | 2 |
| 39.93 | 2.258 | 2 |
| 40.53 | 2.226 | 3 |
| 41.18 | 2.192 | 3 |
| 42.01 | 2.151 | 3 |
| 42.74 | 2.116 | 1 |
| 43.53 | 2.079 | 4 |
| 43.83 | 2.066 | 3 |
| 45.24 | 2.004 | 19* |
| 46.28 | 1.962 | 4 |
| 46.95 | 1.935 | 10 |
| 48.65 | 1.872 | 4 |
| 50.19 | 1.818 | 5 |
| 51.06 | 1.789 | 4 |
| 51.65 | 1.770 | 6 |
| 52.48 | 1.744 | 4 |
| 53.03 | 1.727 | 6 |
| 53.91 | 1.701 | 6 |
| 55.52 | 1.655 | 4 |
| 57.36 | 1.606 | 5 |
| 58.29 | 1.583 | 5 |
| 59.33 | 1.558 | 4 |

In Table 3, * indicates that a shoulder appears on the low 2 Theta side of the peak, and ** indicates that a shoulder appears on the high 2 Theta side of the peak. There was one unresolved peak between d-spacing of 2.442 and 2.411 Angstroms, and the minor amount of impurity remained.

The sorption data obtained on the calcined product of this example was as follows, in weight percent:

| | |
|---|---|
| Cyclohexane | 2.0 |
| n-Hexane | 2.2 |
| Water | 4.8 |

EXAMPLE 2-6

Table 4 presents details of additional examples, including reaction mixture compositions, crystallization conditions, product compositions and sorption test results of calcined (6 hours at 538° C.) products. Alumina was provided by Al$_2$(SO$_4$)$_3$·xH$_2$O and silica was provided by Ultrasil in each example. Alkali metal was potassium in Examples 2, 4 and 6 and sodium in Examples 3 and 5. In Examples 2, 3, 4 and 5 the product was substantially 100% MCM-35 by X-ray analysis. The Example 6 product was MCM-35 with trace ZSM-5 by X-ray analysis.

The X-ray diffraction patterns for the as-synthesized and calcined products of Example 2 included the values shown in Tables 5 and 6, respectively.

TABLE 4

| | Example No. | | | | |
|---|---|---|---|---|---|
| | 2 | 3 | 4 | 5 | 6 |
| Synthesis Mixture, mole ratios | | | | | |
| SiO$_2$/Al$_2$O$_3$ | 140 | 120 | 100 | 70.1 | 50.1 |
| H$_2$O/SiO$_2$ | 20.0 | 17.9 | 20.0 | 19.7 | 20.0 |
| OH$^-$/SiO$_2$ | 0.03 | 0.03 | 0.04 | 0.04 | 0.05 |
| M/SiO$_2$ | 0.05 | 0.08 | 0.10 | 0.13 | 0.17 |
| R/SiO$_2$ | 0.30 | 0.20 | 0.30 | 0.30 | 0.30 |
| Crystallization, Stirred Temp., °C./Days | 175/3 | 160/19 | 175/3 | 175/3 | 175/3 |
| Product Composition, Wt. % | | | | | |
| SiO$_2$ | 86.7 | 88.7 | 89.5 | 83.8 | 85.5 |
| Al$_2$O$_3$ | 1.2 | 1.4 | 1.8 | 2.3 | 3.5 |
| K | 0.37 | — | 0.30 | — | 0.76 |
| Na | — | 0.16 | — | 0.18 | — |
| N | 0.88 | 0.96 | 0.92 | 1.21 | 0.95 |
| Ash | 88.7 | 91.0 | 91.6 | 86.8 | 93.9 |
| SiO$_2$/Al$_2$O$_3$, molar | 123 | 108 | 84.5 | 62.0 | 41.5 |
| Adsorption, Wt. % | | | | | |
| Cyclohexane | 1.7 | 3.4 | 2.2 | 2.1 | 3.4 |
| n-Hexane | 4.6 | 4.7 | 3.0 | 3.2 | 3.8 |
| Water | 3.5 | 3.2 | 3.2 | 4.9 | 6.1 |

TABLE 5

X-RAY DIFFRACTION PATTERN OF AS-SYNTHESIZED EXAMPLE 2 PRODUCT

| Observed 2 Theta | d (A) | Relative Intensity |
|---|---|---|
| 5.70 | 15.50 | 23 |
| 9.73 | 9.09 | 23 |
| 11.47 | 7.71 | 1 |
| 13.38 | 6.62 | 7 |
| 15.30 | 5.79 | 10 |
| 16.65 | 5.33 | 1 |
| 17.32 | 5.12 | 7 |
| 17.76 | 4.99 | 21 |
| 18.65 | 4.76 | 1 |
| 19.49 | 4.55 | 2 |
| 21.17 | 4.20 | 60 |
| 21.94 | 4.05 | 45* |
| 22.24 | 4.00 | 32 |
| 22.74 | 3.91 | 71 |
| 24.26 | 3.67 | 2 |

TABLE 5-continued
X-RAY DIFFRACTION PATTERN OF AS-SYNTHESIZED EXAMPLE 2 PRODUCT

| Observed 2 Theta | d (A) | Relative Intensity |
|---|---|---|
| 24.95 | 3.57 | 44 |
| 25.52 | 3.49 | 100 |
| 25.95 | 3.43 | 25 |
| 26.48 | 3.37 | 12 |
| 26.90 | 3.32 | 20 |
| 27.69 | 3.22 | 6 |
| 28.06 | 3.18 | 14 |
| 28.94 | 3.08 | 3 |
| 29.48 | 3.031 | 11 |
| 30.15 | 2.964 | 9 |
| 32.95 | 2.718 | 3 |
| 31.24 | 2.863 | 5 |
| 31.61 | 2.831 | 10 |
| 32.28 | 2.765 | 2 |
| 33.38 | 2.684 | 5 |
| 34.46 | 2.610 | 2 |
| 34.89 | 2.572 | 1 |
| 35.93 | 2.500 | 3 |
| 36.70 | 2.449 | 4 |
| 37.27 | 2.413 | 7 |
| 37.86 | 2.376 | 4 |
| 38.21 | 2.356 | 2 |
| 39.82 | 2.264 | 2 |
| 40.43 | 2.231 | 2 |
| 41.12 | 2.195 | 2 |
| 41.89 | 2.157 | 4 |
| 43.37 | 2.086 | 4 |
| 45.15 | 2.000 | 20 |
| 46.24 | 1.963 | 4 |
| 46.91 | 1.937 | 10 |
| 48.53 | 1.876 | 4 |
| 50.08 | 1.821 | 4 |
| 50.94 | 1.792 | 3 |
| 51.78 | 1.765 | 5 |
| 52.41 | 1.746 | 4 |
| 52.96 | 1.729 | 6 |
| 53.85 | 1.703 | 5 |
| 55.39 | 1.659 | 4 |
| 57.28 | 1.608 | 5 |
| 58.13 | 1.587 | 5 |
| 59.22 | 1.560 | 4 |

TABLE 6
X-RAY DIFFRACTION PATTERN OF CALCINED EXAMPLE 2 PRODUCT

| Observed 2 Theta | d (A) | Relative Intensity |
|---|---|---|
| 5.73 | 15.43 | 36 |
| 9.77 | 9.05 | 40 |
| 11.44 | 7.73 | 4 |
| 12.08 | 7.33 | 4 |
| 12.69 | 6.98 | 4 |
| 13.40 | 6.61 | 17 |
| 15.33 | 5.78 | 25 |
| 17.25 | 5.14 | 3 |
| 17.78 | 4.99 | 16 |
| 18.70 | 4.75 | 2 |
| 19.54 | 4.10 | 1 |
| 21.23 | 4.18 | 60 |
| 21.75 | 4.09 | 21 |
| 21.99 | 4.04 | 43 |
| 22.32 | 3.98 | 32 |
| 22.77 | 3.91 | 61 |
| 24.31 | 3.66 | 2 |
| 24.99 | 3.56 | 45 |
| 25.58 | 3.48 | 100 |
| 25.96 | 3.43 | 24 |
| 26.51 | 3.36 | 12 |
| 26.98 | 3.31 | 25 |
| 27.73 | 3.22 | 7 |
| 28.11 | 3.17 | 16 |
| 28.99 | 3.08 | 2 |
| 29.55 | 3.02 | 13 |
| 30.09 | 2.969 | 9 |
| 31.26 | 2.861 | 7 |
| 31.66 | 2.826 | 13 |
| 32.51 | 2.754 | 4 |
| 32.99 | 2.715 | 4 |
| 33.44 | 2.680 | 4 |
| 33.81 | 2.651 | 2 |
| 34.46 | 2.603 | 2 |
| 34.97 | 2.566 | 2 |
| 35.99 | 2.496 | 4 |
| 36.80 | 2.442 | 4 |
| 37.12 | 2.422 | 6 |
| 37.35 | 2.407 | 8 |
| 37.86 | 2.376 | 4 |
| 38.34 | 2.348 | 3 |
| 39.26 | 2.294 | 2 |
| 39.87 | 2.261 | 2 |
| 40.50 | 2.227 | 3 |
| 41.03 | 2.200 | 2 |
| 42.01 | 2.150 | 3 |
| 43.66 | 2.073 | 4 |
| 45.25 | 2.004 | 19 |
| 46.33 | 1.960 | 4 |
| 46.98 | 1.934 | 9 |
| 48.63 | 1.872 | 5 |
| 50.13 | 1.820 | 4 |
| 51.10 | 1.787 | 4 |
| 51.75 | 1.767 | 5 |
| 52.05 | 1.726 | 6 |
| 53.92 | 1.700 | 5 |
| 55.48 | 1.656 | 4 |
| 57.37 | 1.606 | 5 |
| 58.21 | 1.585 | 6 |
| 59.33 | 1.558 | 4 |

In Table 5, The * indicates that a shoulder appears on the low 2 Theta side of the peak. In the X-ray pattern of the as-synthesized Example 2 product, there were unresolved peaks between d-spacings of 2.572 and 2.500 Angstroms and between 2.449 and 2.413 Angstroms. In the X-ray pattern of the calcined Example 2 product, there was an unresolved peak between d-spacings of 2.073 and 2.004 Angstroms.

EXAMPLE 7

A portion of the calcined product of Example 1 was ammonium exchanged and calcined at 538° C. for 3 hours to prepare the hydrogen form. It was then tested for catalytic activity by the Alpha test and found to have an Alpha Value of 25.

EXAMPLE 8

A portion of the calcined product of Example 2 was ammonium exchanged, calcined and tested as in Example 7. It had an Alpha Value of 2.

EXAMPLE 9

A portion of the calcined product of Example 5 was ammonium exchanged, calcined and tested as in Example 7. It had an Alpha Value of 38.

EXAMPLE 10

A portion of the calcined product of Example 6 was ammonium exchanged, calcined and tested as in Example 7. It had an Alpha Value of 67.

EXAMPLE 11

Comparative ethylbenzene synthesis reactions were run in an upflow reactor at 800° F., atmospheric pressure and a WHSV of 11 hr$^{-1}$. The molar ratio of benzene/ethylene was maintained at 10. The catalysts comprised zeolite Beta, ZSM-5 and two separate MCM-35 materials. Each catalyst was composed of 35% alumina binder and 65% zeolite. The MCM-35 materials were made in Examples 5 and 6. Each catalyst was activated by calcination in nitrogen at 540° C., followed by aqueous ammonium nitrate exchange and calcination in air at 540° C. Products of the ethylbenzene synthesis reactions included the components listed below in weight percent:

|  | Catalyst | | | |
| --- | --- | --- | --- | --- |
| Component | Beta | ZSM-5 | Example 5 MCM-35 | Example 6 MCM-35 |
| $C_2H_4$ | 0.09 | 0.19 | 0.59 | 0.25 |
| $C_3$ | 0.32 | — | — | — |
| $C_4$ | 0.40 | — | — | — |
| Benzene | 88.51 | 89.24 | 88.15 | 87.07 |
| Toluene | 4.92 | 0.39 | 0.12 | 0.18 |
| Ethylbenzene | 4.24 | 9.68 | 10.58 | 12.05 |
| p-Xylene | 0.18 | 0.21 | — | — |
| $C_9+$ | 1.36 | 0.29 | 0.57 | 0.45 |

What is claimed is:

1. A process for converting feedstock organic compounds to conversion product which comprises contacting said feedstock at conversion conditions including a temperature of from about 0° C. to about 800° C., a pressure of from about 0.1 atmosphere to about 250 atmospheres and a weight hourly space velocity of from about 0.08 $hr^{-1}$ to about 500 $hr^{-1}$, with catalyst comprising a synthetic crystalline material characterized by an X-ray diffraction pattern exhibiting interplanar d-spacing values including those at 15.4±0.23; 9.03±0.14; 6.62±0.10; 4.99±0.07; 4.04±0.05; 3.31±0.04; and 2.00±0.03 Angstroms.

2. The process of claim 1 wherein said crystalline material has a composition comprising the molar relationship $$X_2O_3:(n)YO_2$$

wherein n is at least about 30, X is a trivalent element and Y is a tetravalent element.

3. The process of claim 2 wherein n is from about 40 to about 200.

4. The process of claim 1 wherein said crystalline material has been subjected to ion exchange with replacing ions selected from the group consisting of hydrogen and hydrogen precursors, rare earth metals, and metals of Groups IIA, IIIA, IVA, IB, IIB, IIIB, IVB, VIB and VIII of the Periodic Table of the Elements and mixtures thereof.

5. The process of claim 2 wherein X comprises aluminum and Y comprises silicon.

6. The process of claim 4 wherein said replacing ions comprise hydrogen or a hydrogen precursor.

7. The process of claim 4 wherein said replacing ions comprise metals.

8. The process of claim 1 wherein said catalyst comprises a matrix material comprising alumina, silica, magnesia, zirconia, thoria, beryllia, titania or mixtures thereof.

9. A process for converting a feedstock comprising hydrocarbon compounds to conversion product comprising hydrocarbon compounds of lower molecular weight than feedstock hydrocarbon compounds which comprises contacting said feedstock at conditions sufficient to convert said feedstock to said product with a catalyst composition comprising a synthetic crystalline material characterized by an X-ray diffraction pattern exhibiting interplanar d-spacing values including those at 15.4±0.23; 9.03±0.14; 6.62±0.10; 4.99±0.07; 4.04±0.05; 3.31±0.04; and 2.00±0.03 Angstroms.

10. The process of claim 9 wherein said crystalline material has a composition comprising the molar relationship $$X_2O_3:(n)YO_2$$

wherein n is at least about 30, X is a trivalent element and Y is a tetravalent element.

11. The process of claim 10 wherein n is from about 40 to about 200.

12. The process of claim 9 wherein said crystalline material has been subjected to ion exchange with replacing ions selected from the group consisting of hydrogen and hydrogen precursors, rare earth metals, and metals of Groups IIA, IIIA, IVA, IB, IIB, IIIB, IVB, VIB and VIII of the Periodic Table of the Elements.

13. The process of claim 10 wherein X comprises aluminum and Y comprises silicon.

14. The process of claim 12 wherein said replacing ions comprise hydrogen or a hydrogen precursor.

15. The process of claim 12 wherein said replacing ions comprise metals.

16. The process of claim 9 wherein said catalyst comprises a matrix material comprising alumina, silica, magnesia, zirconia, thoria, beryllia, titania or mixtures thereof.

17. The process of claim 1 wherein said conversion conditions include a temperature of from about 300° C. to about 800° C., a pressure of from about 0.1 atmosphere to about 35 atmospheres and a weight hourly space velocity of from about 0.1 $hr^{-1}$ to about 20 $hr^{-1}$.

18. The process of claim 1 wherein said conversion conditions include a temperature of from about 300° C. to about 700° C., a pressure of from about 0.1 atmosphere to about 10 atmospheres and a weight hourly space velocity of from about 0.1 $hr^{-1}$ to about 20 $hr^{-1}$.

19. The process of claim 9 wherein said conversion conditions include a temperature of from about 300° C. to about 800° C., a pressure of from about 0.1 atmosphere to about 35 atmospheres and a weight hourly space velocity of from about 0.1 $hr^{-1}$ to about 20 $hr^{-1}$.

20. The process of claim 9 wherein said conversion conditions include a temperature of from about 300° C. to about 700° C., a pressure of from about 0.1 atmosphere to about 10 atmospheres and a weight hourly space velocity of from about 0.1 $hr^{-1}$ to about 20 $hr^{-1}$.

21. A process for preparing short chain alkyl aromatic compounds which comprises contacting at least one alkylatable aromatic compound with at least one alkylating agent possessing an aliphatic group having from 1 to 5 carbon atoms under alkylation reaction conditions and in the presence of an alkylation catalyst to provide an alkylated aromatic product possessing at least one alkyl group derived from said alkylating agent, said catalyst comprising a synthetic crystalline material characterized by an X-ray diffraction pattern exhibiting interplanar d-spacing values including those at 15.4±0.23; 9.03±0.14; 6.62±0.10; 4.99±0.07; 4.04±0.05; 3.31±0.04; and 2.00±0.03 Angstroms.

22. The process of claim 21 wherein said synthetic crystalline material has been treated to replace original ions, at least in part, with an ion or mixture of ions selected from the group consisting of hydrogen, hydrogen precursors, rare earth metals and metals of Groups IIA, IIIA, IVA, IB, IIB, IIIB, IVB, VIB and VIII of the Periodic Table.

23. The process of claim 21 wherein said synthetic crystalline material has been thermally treated at a temperature up to about 925° C.

24. The process of claim 22 wherein said synthetic crystalline material has been thermally treated at a temperature up to about 925° C.

25. The process of claim 21 wherein said catalyst comprises a matrix material comprising alumina, silica, magnesia, zirconia, thoria, beryllia, titania or mixtures thereof.

26. The process of claim 21 wherein the alkylating agent is an alpha olefin of from 2 to 5 carbon atoms.

27. The process of claim 21 wherein the alkylating agent is ethylene or propylene.

28. The process of claim 21 wherein the alkylatable aromatic compound is selected from the group consisting of benzene, xylene, toluene, 1,2,3,5-tetramethylbenzene and cumene.

29. The process of claim 21 wherein the alkylatable aromatic compound is selected from the group consisting of naphthalene, anthracene, naphthacene, perylene, coronene and phenanthrene.

30. The process of claim 21 wherein the alkylatable aromatic compound is cumene and the alkylating agent is propylene.

31. The process of claim 21 wherein the alkylation reaction conditions include a temperature of between about 0° C. and about 500° C., a pressure of from about 0.2 to about 250 atmospheres, a WHSV of from about 0.1 $hr^{-1}$ to about 500 $hr^{-1}$ and a molar ratio of alkylatable aromatic compound to alkylating agent of from about 0.1 to about 50.

32. The process of claim 21 wherein the alkylation reaction conditions include a temperature of between about 50° C. and about 250° C., a pressure of from about 1 to about 25 atmospheres, a WHSV of from about 0.5 $hr^{-1}$ to about 100 $hr^{-1}$ and a molar ratio of alkylatable aromatic compound to alkylating agent of from about 0.5 to about 15.

* * * * *